US00RE46402E

(19) United States
(12) Reissued Patent
Grande et al.

(10) Patent Number: US RE46,402 E
(45) Date of Reissued Patent: May 16, 2017

(54) BIOACTIVE SCAFFOLDS

(71) Applicant: The Feinstein Institute For Medical Research, Manhasset, NY (US)

(72) Inventors: Daniel A. Grande, Sea Cliff, NY (US); James M. Mason, Bethpage, NY (US); Arnold S. Breitbart, Great Neck, NY (US)

(73) Assignee: The Feinstein Institute for Medical Research, Manhasset, NY (US)

(21) Appl. No.: 14/994,478

(22) Filed: Jan. 13, 2016

Related U.S. Patent Documents

Reissue of:
(64) Patent No.: 9,089,117
Issued: Jul. 28, 2015
Appl. No.: 12/322,262
Filed: Jan. 30, 2009

U.S. Applications:
(63) Continuation-in-part of application No. PCT/US2007/017242, filed on Aug. 1, 2007.

(60) Provisional application No. 60/834,682, filed on Aug. 1, 2006.

(51) Int. Cl.

| | |
|---|---|
| ***A01K 67/027*** | (2006.01) |
| ***A61K 38/30*** | (2006.01) |
| ***A61K 38/18*** | (2006.01) |
| ***A61L 27/56*** | (2006.01) |
| ***A61L 27/38*** | (2006.01) |
| ***A61K 47/48*** | (2006.01) |

(52) U.S. Cl.
CPC ..... *A01K 67/0271* (2013.01); *A61K 38/1841* (2013.01); *A61K 38/1858* (2013.01); *A61K 38/1875* (2013.01); *A61K 38/30* (2013.01); *A61K 47/48776* (2013.01); *A61L 27/38* (2013.01); *A61L 27/56* (2013.01)

(58) Field of Classification Search
CPC ..... A01K 67/0271
See application file for complete search history.

(56) References Cited

U.S. PATENT DOCUMENTS

| | | | | |
|---|---|---|---|---|
| 5,763,416 | A | 6/1998 | Bonadio | |
| 6,398,816 | B1 * | 6/2002 | Breitbart | A61K 38/1875 424/422 |
| 7,252,982 | B2 | 8/2007 | Madry et al. | |
| 7,767,221 | B2 * | 8/2010 | Lu et al. | 424/423 |
| 2003/0009235 | A1 * | 1/2003 | Manrique et al. | 623/23.63 |
| 2004/0156878 | A1 * | 8/2004 | Rezania et al. | 424/423 |
| 2010/0008967 | A1 | 1/2010 | Grande et al. | |

OTHER PUBLICATIONS

PCT International Search Report dated May 9, 2008 in connection with PCT International Patent Application No. PCT/US2007/17242, 5 pages.

* cited by examiner

*Primary Examiner* — Johnny F Railey
(74) *Attorney, Agent, or Firm* — Amster, Rothstein & Ebenstein LLP

(57) ABSTRACT

Provided are tissue scaffolds colonized by vertebrate cells expressing, a transgenic bioactive molecule, where the vertebrate cells are unable to undergo mitosis. Also provided are methods of growing tissue in a mammal and methods of delivering a transgenic bioactive molecule to a tissue of a mammal, using the tissue scaffolds. Additionally, methods of making the tissue scaffolds are provided.

33 Claims, 4 Drawing Sheets

BIOACTIVE SCAFFOLDS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

This application is a continuation-in-part of PCT Application No. PCT/US2007/017242, filed Aug. 1, 2007, which claims the benefit of U.S. Provisional Application No. 60/834,682, filed Aug. 1, 2006, the contents of both of which are hereby incorporated by reference in their entirety.

BACKGROUND OF THE INVENTION (1) Field of the invention

The present invention generally relates to tissue engineering. More specifically, the invention is directed to improved tissue scaffolds that comprise transgenic bioactive molecules.

(2) Description of the Related Art

Tissue engineering using scaffolds seeded with vertebrate cells are widely used to produce varied tissues that are utilized in vivo. Scaffolds can be used to make numerous tissue types including vascular tissue (US Patent Application Publication 2003/0068817), cardiac or skeletal muscle, nervous tissue (US Patent Application Publication 2004/0078090), skin (WO99/43787), and others (See, e.g., US Patent Application Publications 2004/0175366, 2004/0078090 and US 2003/0068817, and PCT Publications WO99/43787, WO03/041568, WO03/044164, and WO03/082145). Scaffolds for various connective tissues (e.g., bone, cartilage, tendon, meniscus, fibrocartilage and ligament) are particularly well developed (Sharma and Elisseeff, 2004; Frenkel and DiCesare, 2004; Almarza and Athanasiou, 2004; U.S. Pat. Nos. 6,737,053; 6,214,369; 6,398,816; 5,906,934; 5,700,289; 4,846,835; PCT Publication WO03/043486).

Further development of tissue engineering methods is particularly needed for rotator cuff tears. Rotator cuff tears are a very common cause of pain and disability. The tendon stabilizes the shoulder by holding the head of the humerus in the glenoid cavity of the scapula (Dahlgren et al., 2001). Occupational shoulder injuries are one of the most frequent patient complaints, second only to back pain (Soslowsky et al., 1997). Among the tendons of the rotator cuff of the shoulder, the supraspinatus tendon is the one often most affected (Thomopoulos et al., 2002). Even though the incidence of rotator cuff tear and shoulder injury is high, the pathophysiology of rotator cuff injury and healing is poorly understood.

Tendon architecture consists of collagen fibrils embedded in a matrix of proteoglycan (Wada et al., 2001). Fibroblasts are the predominant cell type within tendons, and they are arranged in spaces between the parallel collagen bundles (Soslowsky et al., 1997; Abboud and Soslowsky, 2002). The major constituent of tendon is type 1 collagen (Wada et al., 2001). During the first week of tendon healing, proliferating tissue from the paratenon penetrates the gap between the tendon stumps and fills it with undifferentiated and disorganized fibroblasts. Capillary buds invade the area and together with the fibroblasts compose the granulation tissue between the tendon ends. Collagen synthesis can be detected by the third day. After about two weeks, the tendon stumps appear to be fused by a fibrous bridge. Dramatic fibroblast proliferation and collagen production in the granulation tissue continue. Between the third and fourth weeks, fibroblasts and collagen fibers near the tendon begin to orient themselves along the long axis Of the tendon as a result of stress. Only collagen near the tendon reorganizes, the more distant scar-like tissue remains unorganized (Wada et al., 2001).

To date, there is no ideal treatment method for rotator cuff healing. The endogenous healing is poor or insufficient in most rotator cuff tears and especially in large massive tears (Carpenter et al., 1998; Skutek et al., 2001). The current technique of suturing the parts of the tendon together does not give the desired improvement in outcome (Skutek et al., 2001). Ideally the best strategy would be one that potentiates endogenous healing processes. Recently, there have been many studies dealing with the properties of the rotator cuff tendon and its intrinsic healing properties (Kobayashi et al., 2001; Thomopoulos et al., 2002; Choi et al., 2002; Premdas et al., 2001; Desmouliere et al., 1993; Nakase et al., 2002; Aspenburg and Forslund, 1999). Kobayashi et al. showed that in the healing of full-thickness tears of avian supracoracoid tendon, the expression of $\alpha$1(III) lasted longer than $\alpha$1(I) procollagen mRNA (Kobayashi et al., 2001). Additionally, the healing process progresses from the bursal side to the joint side (Kobayashi et al., 2001; Premdas et al., 2001). This was shown in an experimentally created full thickness tear of rotator cuff tendon (Kobayashi et al., 2001). In a rat model study, it was noted that type XII collagen, aggrecan and biglycan was also increased in the healing tissue (Thomopoulos et al., 2002). Type XII collagen is fibril-associated collagen that binds to type I collagen and projects into ground matrix (Thomopoulos et al., 2002). In an acute supraspinatus tendon model tear in rabbits, it was shown that matrix metalloprotinease (MMP-2), a collagen degrading enzyme, may inhibit the healing process (Choi et al., 2002). Tissue inhibitor matrix metalloprotinease 1 (TIMP-I), the inhibitor of the MMP family, seems to enhance healing suggesting that inadequate TIMP-I is responsible for poor healing (Choi et al., 2002). However, the most interesting finding was that a large percentage of fibroblasts in the torn human rotator cuff contain smooth muscle actin (SMA) (Premdas et al., 2001). TGF-$\beta$1 increases the level of SMA, and thereby fibroblasts, in these tissues. Myofibroblasts have been proposed to play a role in wound contracture and retractile phenomenon observed during the fibrotic process (Desmouliere et al., 1993; Abboud and Soslowsky, 2002). Cartilage-derived morphogenic protein 1 (CDMP 1), a member of the bone morphogenic protein (BMP) superfamily has been identified as having chondrogenic activity (Nakase et al., 2002; Aspenburg and Forslund, 1999). In addition, GDF-5, the mouse homologue of CDMP-I reportedly induces the development of tendon tissue in vivo when implanted ectopically and enhances tendon healing in rats (Nakase et al., 2002; Aspenburg and Forslund, 1999). The pattern of localization of GDF-5 was found to be similar to that of collagen 1 (Col 1) messenger RNA (mRNA) Nakase et al., 2002; Aspenburg and Forslund, 1999). In light of these studies, it is possible that the combination of GDF-5 and TGF-$\beta$ may play a crucial role in the healing process. Theoretically, GDF-5 will induce the development of tendon tissue by specifically directing the synthesis of collagen. TGF-β, meanwhile, will induce contractile activity and thereby, proliferate the reparative process.

Surgically demonstrable full thickness tears are present in about ⅕th of all elderly patients. The etiology of the tear includes impingement syndrome, instability, trauma, etc. (Malickey et al., 2002; Lewis et al., 2001). Impingement syndrome, which constitutes 75% of rotator cuff etiology, describes pain in the subacromial space when the humerus is elevated or internally rotated (Malickey et al., 2002; Rickert et al., 2001). During humeral flexion, the supraspinatus tendon and bursa become entrapped between the antero inferior corner of the acromion (and coraco-acromial ligament) and the greater tuberosity (Carpenter et al., 1998). This syndrome is thought to precipitate attritional changes in the rotator cuff, leading to rotator cuff tear (Carpenter et al, 1998; Bey et al., 2002). Once the supraspinatus (and infraspinatus) tendon is disrupted there will often be further impingement and irritation, which can lead to biceps tendonitis and subsequent rupture (Carpenter et al., 1998). Shoulder instability could be anterior or multidirectional (Carpenter et al., 1998). In either case, it happens to young active athletes that are involved overhead throwing sports. Non-operative treatment for minor rotator cuff tears includes rest and gentle stretch and strengthening (Jann et al., 1999). The current gold standard for rotator cuff tear, however, is surgical repair of tendon (Carpenter et al., 1998). Animal models have been developed for both tendon and ligament tissue engineering (Carpenter et al., 1999).

Cells seeded onto scaffolds generally do not produce sufficient cytokines to provide for optimum growth and colonization of the scaffold, improved colonization of the scaffold can be achieved by utilizing cells that are genetically engineered to produce increased cytokine levels. See, e.g., U.S. Pat. No. 6,398,816. However, transplantation of scaffolds comprising viable transgenic cells can lead to problems such as excessive production of the transgenic cytokines and/or spread and growth of the transgenic cells away from the transplanted area.

Thus, there is a need for improved methods for utilizing transgenic cells on scaffolds for tissue engineering. The present invention addresses that need.

SUMMARY OF THE INVENTION

Accordingly, the inventors have discovered that scaffolds comprising cells expressing a transgenic bioactive molecule are advantageously treated such that the cells are rendered unable to undergo mitosis.

Thus, in some embodiments, the invention is directed to tissue scaffolds colonized by vertebrate cells expressing a first transgenic bioactive molecule, where the vertebrate cells are unable to undergo mitosis.

In other embodiments, the invention is directed to methods of growing tissue in a mammal. The methods comprise implanting the above-described tissue scaffold into the mammal.

Additionally, the invention is directed to methods of delivering a first transgenic bioactive molecule to a tissue of a mammal. The methods comprise implanting the above-described tissue scaffold into the mammal in or adjacent to the tissue.

In further embodiments, the invention is directed to methods of making the above-described tissue scaffold. The methods comprise seeding a scaffold with vertebrate cells comprising a transgene encoding bioactive molecule, incubating the scaffold under conditions and for a time sufficient for the cells to colonize the scaffold and express the transgenic bioactive molecule, then treating the cells colonizing the scaffold such that the cells are unable to undergo mitosis.

The invention is also directed to the use of any of the above invention tissue scaffolds for controlling tissue growth in a mammal.

Further, the invention is directed to the use of any of the above invention the tissue scaffolds for delivering the first transgenic bioactive molecule to a mammal.

DETAILED DESCRIPTION OF THE INVENTION

Figure 1:
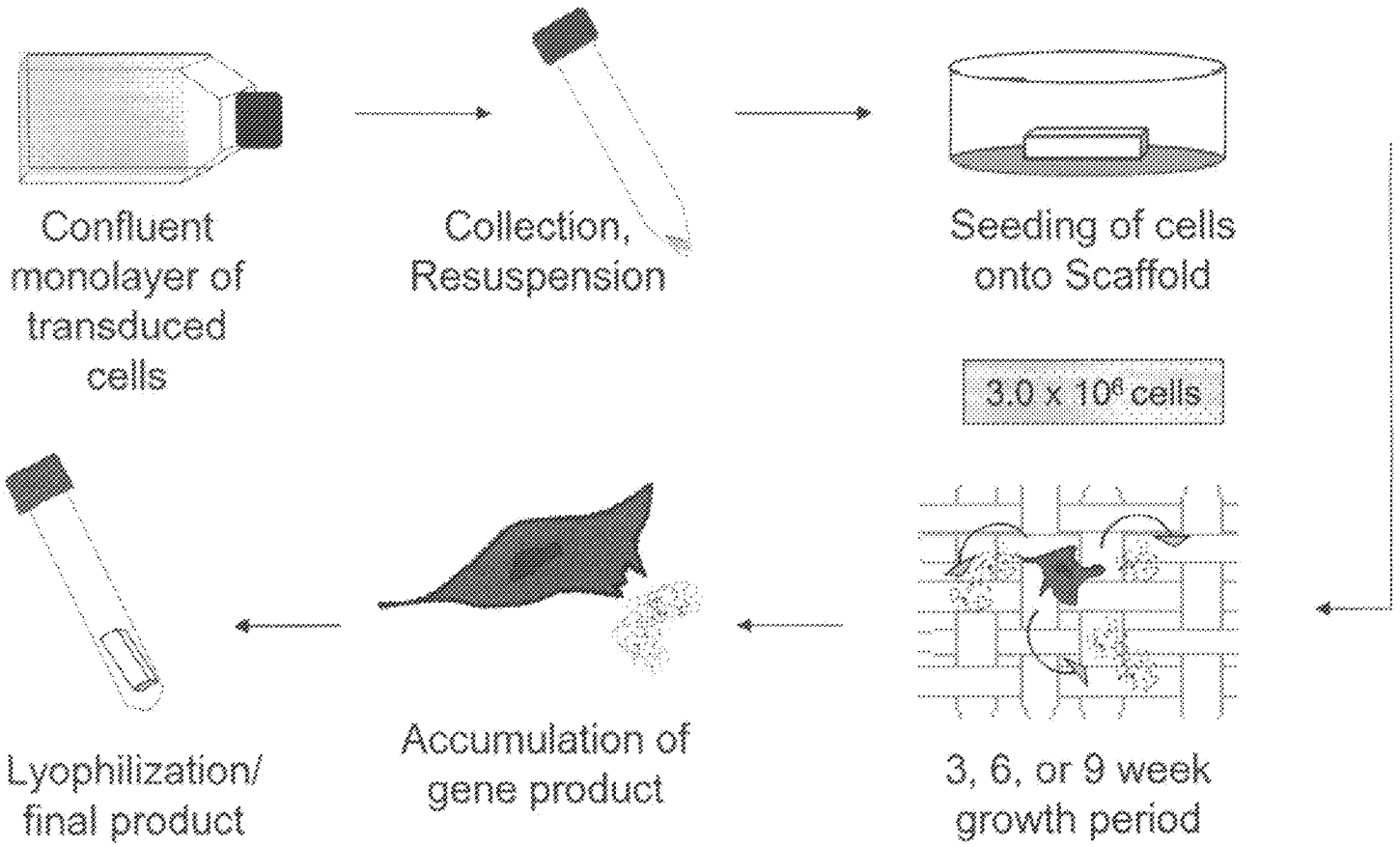
FIG. 1 is an illustration of an in vitro model of an embodiment of the invention.

The inventors have discovered that scaffolds comprising cells expressing a transgenic bioactive molecule are advantageously treated such that the cells are rendered unable to undergo mitosis. The nondividing cells are unable to further colonize the scaffold, or multiply at a site away from the scaffold. In some embodiments, the cells of the scaffold are killed, wherein the cells then become a slow release source of the transgenic bioactive molecule.

As used herein, "allogenic tissue" or "allogeneic cell" refers to a tissue or cell that is isolated from an individual and used in another individual of the same species. The term "xenogeneic tissue" or "xenogeneic cell" refers to a tissue or cell that is isolated from art individual of one species and placed in an individual of another species. The term "autogeneic tissue" or "autogenic cell" refers to a tissue or cell that is isolated from an individual and grafted back into that same individual.

As used herein, "transgenic" refers to art organism in which DNA has been artificially introduced, or a compound that is produced in the organism encoded by the DNA that has been artificially introduced. The transgenic compound can be the DNA itself, RNA transcribed from the DNA, a protein that has been translated from the DNA, or combinations thereof.

As used herein, a cytokine is a protein that is secreted by various vertebrate cells and that can affect growth or maturation of cells (e.g., a growth factor), or influence inflammatory responses.

In some embodiments, the invention is directed to tissue scaffolds colonized by vertebrate cells expressing a first transgenic bioactive molecule. In these embodiments, the vertebrate cells are unable to undergo mitosis.

The vertebrate cells can be rendered unable to undergo mitosis by any means known in the art, e.g., sublethal chemical or radiation treatment. Preferably, the vertebrate cells are dead. In those embodiments, the cells can be killed by any means, including, treatment with a cytotoxin, a lethal radiation treatment, or, preferably freezing then preferably thawing.

In some preferred embodiments, the vertebrate cells are killed, then the scaffold is preserved for later implantation, e.g., by freezing, or, preferably, lyophilizing. The cells can also be killed by lyophilization.

The invention is not narrowly limited to any particular class of transgenic bioactive molecule. The molecule can be a protein or peptide (e.g., an enzyme, a cytokine, a structural protein such as collagen, an antibody or other protein comprising an antibody binding site, a hormone, a detectable protein such as green fluorescent protein, a chimeric or fusion protein, a protein having a general systemic metabolic function, such as factor VIII, a virus such as a vector, etc.), a nucleic acid (e.g., a ribozyme, an antisense molecule, an aptamer, an siRNA, etc.) or a combination (e.g., a virus). Bioactive fragments of these molecules are also included. The bioactive molecule will typically be not normally expressed in the cells, although they can also be molecules that are expressed but in different quantities, with different activities, or under the control of different mechanisms controlling expression. The vertebrate cells can also express a second, third, fourth, etc. transgenic bioactive molecule.

In preferred embodiments, the transgenic bioactive molecule is a protein that enhances the temporal sequence of wound repair, alters the rate of proliferation, increases the metabolic synthesis of extracellular matrix proteins, or directs phenotypic expression in endogenous cell populations. Examples include cytokines and structural proteins. In various preferred embodiments, the bioactive molecule is a bone growth factor, a nerve growth factor, a cartilage growth factor, a fibroblast growth factor, a skeletal growth factor, an osteoblast-derived growth factor, a growth factor affecting wound healing, or a growth factor affecting tissue repair. Specific examples of bioactive molecules include pleiotrophin, endothelin, tenascin, fibronectin, fibrinogen, vitronectin, V-CAM, I-CAM, N-CAM, selectin, cadherin, integrin, larninin, actin, myosin, collagen, microfilament, intermediate filament, elastin, fibrillin, platelet-derived growth factor (PDGF), vascular endothelial growth factor (VEGF), epidermal growth factor (EGF), basic fibroblast growth factor (FGF), insulin-like growth factor (IGF), endothelial derived growth supplement (EDGS), cartilage-derived morphogenic protein, hepatocyte growth factor, keratinocyte growth factor (KCF), osteogenin, skeletal growth factor (SGF), bone-derived growth factors (BDGFs), retinoids, growth hormone (GH), bone morphogenic proteins (BMPs) including BMP2 to BMP 15, a transcription factor, a member of the hedgehog family, and transferrin. In some more preferred embodiments, the bioactive molecule is a bone morphogenic protein (BMP), TGFβ, or an insulin-like growth factor (IGF). In other more preferred embodiments, the first bioactive molecule is PDGF-β or IGF-1.

One or more than one bioactive molecule can also be incorporated into the scaffold extracellularly either before, during or after colonization of the scaffold by the vertebrate cells. These extracellular bioactive molecules can be any of the above-described bioactive molecules, or any other useful bioactive molecule, e.g., compounds that cannot be encoded genetically, such as compounds or agents that prevent infection (e.g., antimicrobial agents and antibiotics), compounds or agents that reduce inflammation (e.g., anti-inflammatory agents), compounds that prevent or minimize adhesion formation, such as oxidized regenerated cellulose (e.g., INTERCEED and SURGICEL, available from Ethicon, Inc.), glycoproteins, glycosaminoglycans (e.g., heparin sulfate, heparin, chondroitin sulfate, dermatan sulfate, keratan sulfate, hyaluronic acid), analgesics, and compounds or agents that suppress the immune system (e.g., immunosuppressants). Cells that are unable to colonize the scaffold, such as platelets, can also be incorporated into the scaffold.

Vertebrate cells from any species can be used in these scaffolds. It is preferred that the vertebrate cells are from the same species as the intended recipient of the scaffold (allogenic or autogenic), although xenogeneic transplants are also envisioned as within the scope of the invention. More preferably, the cells are from the intended recipient (autogenic), although this may be impractical for many applications, since the cells must be taken from the recipient, transfected with the gene for the transgenic bioactive molecule, cultured on the scaffold for days or weeks, and then rendered unable to undergo mitosis before implantation of the scaffold into the recipient. For most purposes, the vertebrate cells are preferably mammalian cells, and most preferably human cells.

The invention is not narrowly limited to the use of any particular cell type. The skilled artisan can select an appropriate cell type for any particular application without undue experimentation. Cell type will typically be selected based on the tissue to be repaired or formed. For example, chondrocytes or fibroblasts can be selected to form cartilage; muscle cells to form muscle. Undifferentiated, or less differentiated, cells may be preferred in some situations. Representative of these cell types include stem cells and mesenchymal cells. Reprogrammed cells may also be used (see, e.g., Li et al., 2005). In a preferred embodiment, mesenchymal cells are obtained from periosteum, then genetically engineered.

Specific examples of cells that can be used to aid healing, repair or formation of bone include osteocytes/osteoblasts and periosteal cells, particularly in combination with the use of the bioactive molecule BMP-2-15 and/or IGF, made by the cells transgenically, or added extracellularly to the scaffold. Specific examples of cells that can aid healing, repair or formation of cartilage include chondrocytes and periosteal cells, particularly in combination with CGF and/or TGFβ. Specific examples of cells that can aid healing, repair or formation of skin include dermal and epidermal cells, particularly in combination with PDGF, VEGF, IGF, and/or GH. Specific examples of cells that can aid healing, repair or formation of nervous tissue include nerve cells and support cells, particularly in combination with NGF. In some cases, cells will be obtained from a tissue biopsy, which is digested with collagenase or trypsin to dissociate the cells. Alternatively, cells can be obtained from established cell lines or from embryonic cell sources. In preferred embodiments for most applications, the cells are nerve cells, epidermal cells, dermal cells, periosteal cells, epithelial cells, endothelial cells, tendon cells, embryonic stem cells, adult stem cells, myoblasts, osteoblasts, chondrocytes, or fibroblasts.

The scaffolds used in the tissue scaffolds of the present invention can be made from any material known for that purpose, which can be derived from a vertebrate or be artificially synthesized.

The materials for use in the scaffold must meet the mechanical and biochemical parameters necessary to provide adequate support for the cells with subsequent growth and proliferation. The materials can be characterized with respect to mechanical properties such as tensile strength using, e.g., an Instron tester, for polymer molecular weight by, e.g., gel permeation chromatography (GPC), glass transition temperature by, e.g., differential scanning calorimetry (DSC) and bond structure by, e.g., infrared (IR) spectroscopy. Toxicology can also be tested by initial screening tests involving Ames assays and in vitro teratogenicity assays, and implantation studies in animals for immunogenicity, inflammation, release and degradation studies, as are known in the art.

In some embodiments, the scaffold can be formed using tissue grafts, such as may be obtained from autogeneic tissue, allogeneic tissue and xenogeneic tissue. By way of non-limiting example, tissues such as skin, cartilage, ligament, tendon, periosteum, perichondrium, synovium, fascia, mesenter and sinew can be used as tissue grafts to form the biocompatible scaffold. In some embodiments where an allogeneic tissue is used, tissue from ad-fetus or newborns can be used to avoid the immunogenicity associated with some adult tissues.

In other embodiments, the scaffolds can be formed from a biocompatible polymer, including bioresorbable or bioabsorbable materials, reinforcing materials (e.g., woven, knitted, warped knitted, non-woven, or braided structures), natural polymers (e.g., fibrin-based materials, collagen-based materials, hyaluronic acid-based materials, glycoprotein-based materials, cellulose-based materials, silks and combinations thereof), biocompatible ceramic material, polymeric foam, and non-bioabsorbable materials (e.g., biocompatible metals such as stainless steel, cobalt chrome, titanium and titanium alloys, bioinert ceramic particles and bioinert polymers). All of the above materials are known in the art as useful scaffolding materials. See, e.g., US Patent Application Publication 2004/0078090 and U.S. Pat. No. 6,398,816. Scaffolds that are a combination of a tissue graft and a biocompatible polymer are also within the scope of the invention.

In preferred embodiments, the scaffold comprises collagen, alginate, chitosan, poly(paradioxanone), poly(lactic acid) (PLA) also known as poly(L-lactic acid) (PLLA)), poly(glycolic acid) (PGA), and/or a copolymer of poly (lactic acid) and poly(glycolic acid) (PLA/PGA).

The vertebrate cells can be transfected using any appropriate means, including viral or plasmid vectors, using chemical transfectants, or physico-mechanical methods such as electroporation and direct diffusion of DNA. See, e.g., U.S. Pat. No. 6,398,816 and references cited therein.

The invention tissue scaffolds can be further seeded with living cells, for use after rendering the vertebrate cells unable to undergo mitosis. In some embodiments, these living cells are capable of mitosis, so they can colonize the area where the scaffold is implanted. Optionally, the living cells can then be allowed to colonize the scaffold in vitro. In preferred embodiments, these additional vertebrate cells are stimulated to grow by the transgenic bioactive molecule, for example to facilitate tissue engineering applications, including tissue repair or regeneration.

These living cells can optionally also express an additional transgenic bioactive molecule. The additional transgenic bioactive molecule can be any of those previously described (e.g., a protein, nucleic acid, or combination). In some embodiments where the additional transgenic bioactive molecule is a protein, it is preferably an enzyme, a cytokine, a marker protein or an antibody. In other embodiments where the additional transgenic bioactive molecule is a nucleic acid, it is preferably an RNAi molecule, a ribozyme, an antisense molecule, or an aptamer. A virus is also envisioned as an additional transgenic bioactive molecule. The additional transgenic bioactive molecule in these embodiments can be constitutively expressed or operably linked to an inducible promoter, where it can be expressed only under specified conditions. Numerous examples of inducible promoters are known in the art.

The present invention is also directed to methods of controlling tissue growth in a mammal. The methods comprise implanting any of the above-described tissue scaffolds into the mammal. When implanted into the mammal, the transgenic bioactive molecule becomes available to the surrounding tissue. In some preferred embodiments, this results in more rapid and/or better-structured scaffold colonization from the surrounding tissue, e.g., when the transgenic bioactive molecule is a cytokine or a vector encoding a cytokine. As used herein, "controlling tissue growth" includes promoting growth or controlling the type of tissue formed during growth.

In other preferred embodiments, the transgenic bioactive molecule is a nucleic acid or viral vector that is taken up by the surrounding cells, transfecting those cells. These embodiments can be utilized to, e.g., supply a protein or nucleic acid to the mammal that is inadequate or missing in the mammal, such as a missing enzyme in a genetic disease. These embodiments can also be utilized to synthesize an antibody or aptamer with a particular specificity, or a ribozyme antisense or RNAi molecule that reduces or eliminates expression of a protein.

The vertebrate cells on the scaffold can come from a different or, preferably, the same species as the mammal. In the most preferred embodiments, to avoid unwanted immune responses to the scaffold, the vertebrate cells are cells derived from the mammal itself.

The mammal can be of any species, including humans.

The invention is not limited to the growth of any particular tissue, and could be utilized for any tissue to which scaffolds can be made. See, e.g., U.S. Patent Publications 2004/0078090, 2003/0211130, and 2003/0068817; PCT Patent Publications WO99/43787, and WO03/041568; and U.S. Pat. No 6,737,053, all incorporated by reference. Non-limiting examples include cartilage tissue, meniscal tissue, ligament tissue, tendon tissue, skin tissue, bone tissue, muscle tissue, periosteal tissue, pericardial tissue, synovial tissue, nerve tissue, fat tissue, kidney tissue, bone marrow, liver tissue, bladder tissue, pancreas tissue, spleen tissue, intervertebral disc tissue, embryonic tissue, periodontal tissue, vascular tissue, blood and combinations thereof.

These methods are particularly suited for growing connective tissue in the mammal. Preferred examples of connective tissues suitable for growth using these methods are bone, cartilage, tendon, meniscus, fibrocartilage and ligament.

In particularly preferred embodiments, the connective tissue is tendon. In these embodiments, preferred first transgenic bioactive molecules are PDGF-β or IGF-1, since those molecules support improved scaffold colonization. See Example.

In other embodiments, the invention is directed to methods of delivering a first transgenic bioactive molecule to a tissue of a mammal. The methods comprise implanting the above-described tissue scaffold into the mammal in or adjacent to the tissue. In these embodiments, the scaffold allows the slow-release of the transgenic bioactive molecule, assuring exposure of the tissue to the transgenic bioactive molecule continuously for an extended time period.

These embodiments are not limited to utilizing any particular transgenic bioactive molecule. Where the purpose of the transgenic bioactive molecule is to stimulate growth, remodeling, or repair of the tissue, the first transgenic bioactive molecule is preferably a bone growth factor, a nerve growth factor, a cartilage growth factor, a growth factor affecting wound healing, or a growth factor affecting tissue repair.

In some preferred embodiments, the tissue is a connective tissue, e.g., bone, cartilage, tendon or ligament. Where the connective tissue is tendon, the first transgenic bioactive molecule is preferably PDGF-β or IGF-1.

In other embodiments, the scaffold further comprises living cells seeded onto the scaffold after the death of the vertebrate cells. These living cells may or may not themselves express an additional transgenic bioactive molecule, such as a protein or a nucleic acid. Where the additional transgenic bioactive molecule is a protein, it can be, for example, an enzyme, a cytokine, a marker protein or an antibody. Where the additional transgenic bioactive molecule is a nucleic acid, it can be, for example, an RNAi molecule, a ribozyme, an antisense molecule, and an aptamer. Further, the additional transgenic bioactive molecule can be constitutively expressed or operably linked to an inducible promoter, and the living cells can be capable or mitosis or not.

The invention is also directed to methods of making the above-described tissue scaffold. The methods comprise seeding a scaffold with vertebrate cells comprising a transgene encoding bioactive molecule, incubating the scaffold under conditions and for a time sufficient for the cells to colonize the scaffold and express the transgenic bioactive molecule, then treating the cells colonizing the scaffold such that the cells are unable to undergo mitosis. In some preferred embodiments the treatment kills the cells, for example with freezing and thawing, preferably followed by lyophilization of the scaffold.

These methods can also comprise subsequent seeding with additional vertebrate cells that are alive. As described above in the context of the tissue scaffold compositions, these additional vertebrate cells preferably advantageously utilize the transgenic bioactive molecule available from the vertebrate cells.

Preferably, either the vertebrate cells or the additional vertebrate cells, or both, are mammalian cells, most preferably human cells.

The invention is also directed to the use of any of the above invention tissue scaffolds for controlling tissue growth in a mammal. The scope of the uses encompassed in these embodiments is no narrower than the methods of controlling tissue growth in a mammal described above.

Further, the invention is directed to the use of any of the above invention the tissue scaffolds for delivering the first transgenic bioactive molecule to a mammal. The scope of the uses encompassed in these embodiments is no narrower than the methods of delivering the first transgenic bioactive molecule to a mammal described above.

Preferred embodiments of the invention are described in the following examples. Other embodiments within the scope of the claims herein will be apparent to one skilled in the art from consideration of the specification or practice of the invention as disclosed herein. It is intended that the specification, together with the example, be considered exemplary only, with the scope and spirit of the invention being indicated by the claims which follow the examples.

Example 1

Tendon Cell-Conditioned Tissue Scaffold

The aim of this study was to assess the metabolic response of freshly seeded tendon cells into a cell-free scaffold conditioned by IGF-1 or PDGF transduced cells.

The growth factors and their genes used in this example are extrapolated from previous in vitro studies that suggest a potential role for use in gene delivery strategies and tendon repair. PDGF-β has been shown to stimulate DNA and matrix synthesis (Kobayashi et al., 2001) especially in stretched tendon cells (Yoshikawa and Abrahamson, 2001). PDGFβ also resulted in a 2-3-fold increase in expression of cell surface integrins (Dahlgren et al., 2002). Integrins such as fibronectin are important mediators of cell attachment and angiogenesis, which would be critical to augmenting, repair.

IGF-1 administered by direct injection was shown to reduce swelling and lesion size and increase cell proliferation, collagen content and stiffness in a model of collagenase-induced flexor tendonitis (Hardwood et al., 1999). Other studies have shown IGF-1 increases collagen and glycosaminoglycan (GAG) synthesis, as well as DNA content suggesting a potent anabolic response (Dahlgren et al., 2001). Further, there is speculation that IGF-1 could enhance tendon repair if delivered locally (Jann et al., 1999).

An in vitro method for testing embodiments of the present invention was developed. Transduced tendon cells expressing PDGF IGF-1 were seeded into polymer scaffolds as illustrated in FIG. 1, and allowed to grow for 3, 6, or 9 weeks. After the specified culture period cells were killed by freezing and lyophilization. The bioactive scaffolds were then seeded with naive non-transduced tendon cells and measured for rate of collagen synthesis and DNA synthesis. Controls included tendon cells alone for preconditioning minus the engineered gene.

Figure 2:
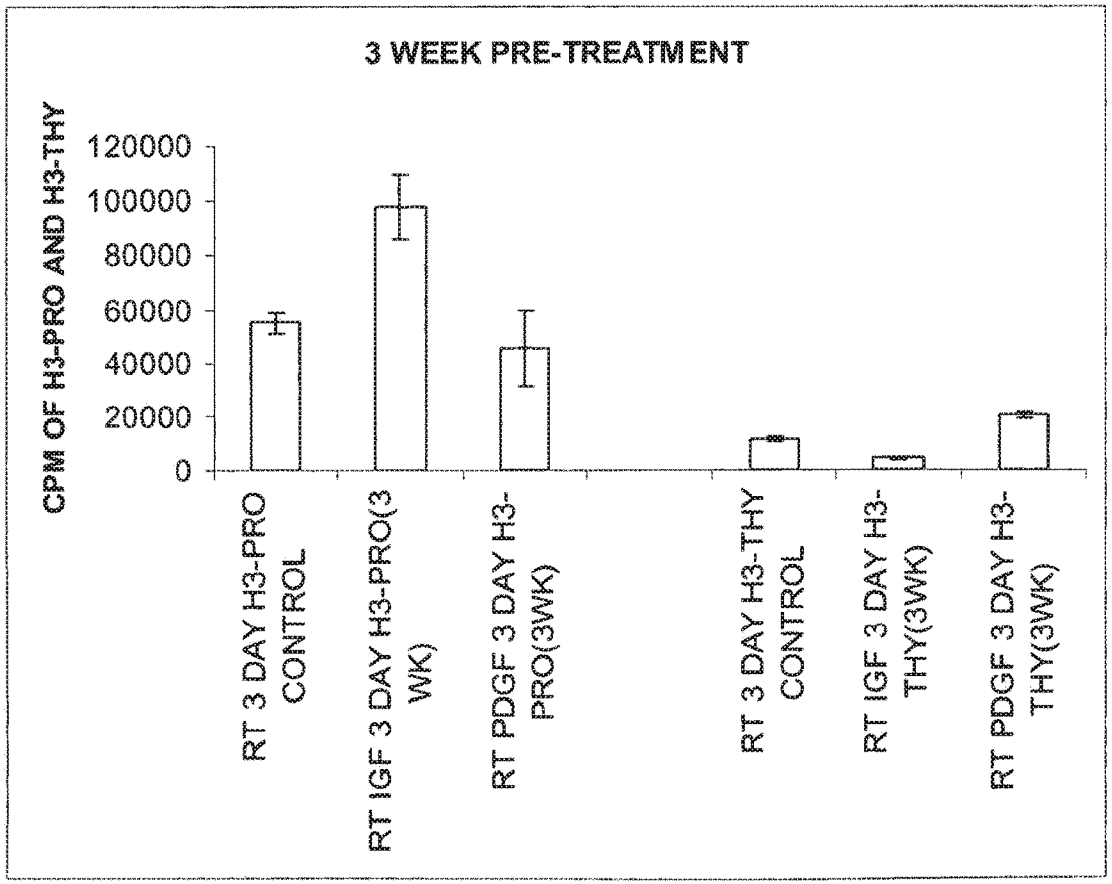
FIG. 2 is a graph showing measurements of collagen (as $^3$H-proline) and DNA (as $^3$H-thymidine) synthesis in naive tendon cells seeded and grown for three days on a scaffold containing killed tendon cells that were transduced with an IGF-1 gene ("IGF"), or a PDGF gene ("PDGF") or no gene ("CONTROL") and grown on the scaffold or three weeks.
Figure 3:
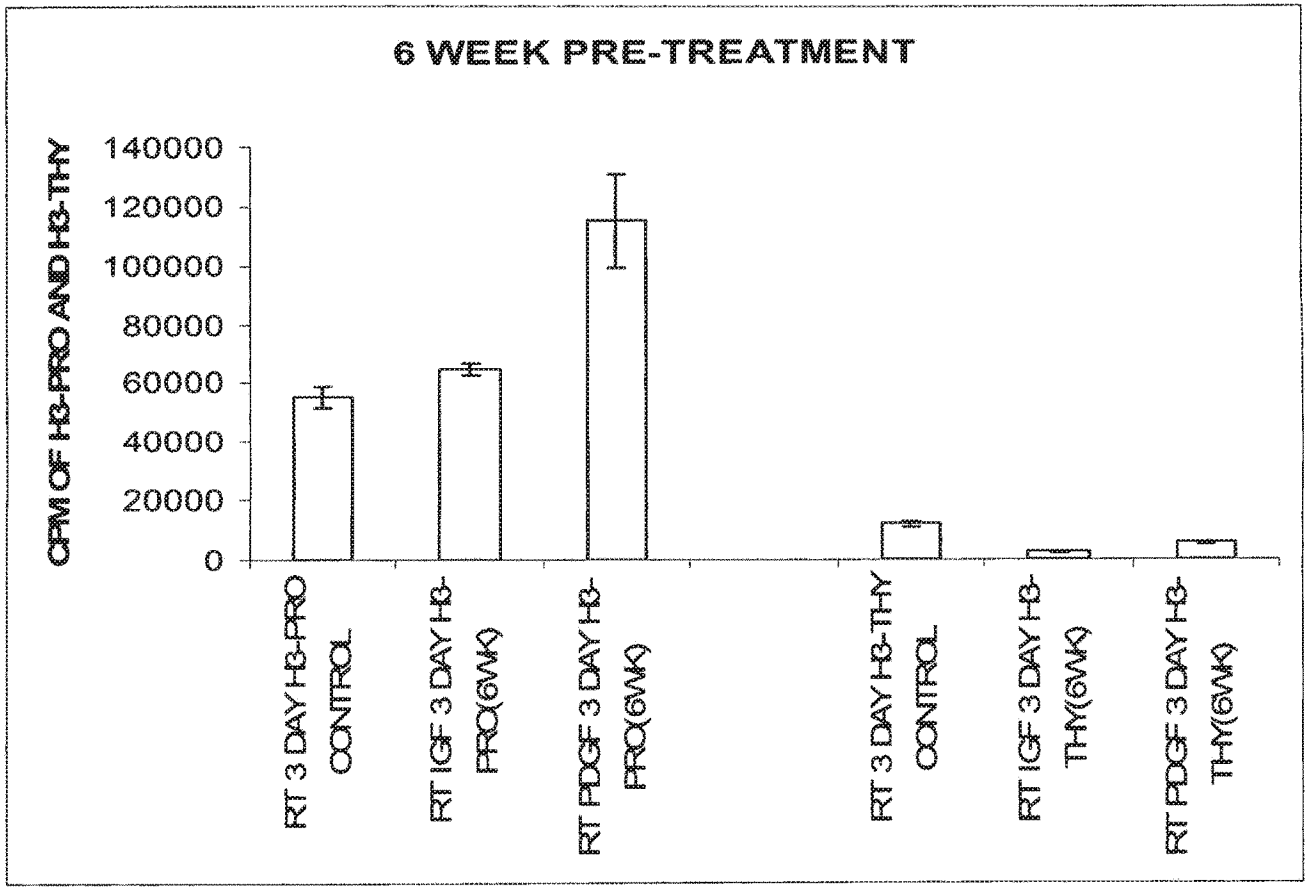
FIG. 3 is a graph showing measurements of collagen (as $^3$H-proline) and DNA (as $^3$H-thymidine) synthesis in naive tendon cells seeded and grown for three days on a scaffold containing killed tendon cells that were transduced with an IGF-1 gene ("IGF"), or a PDGF gene ("PDGF") or no gene ("CONTROL") and grown on the scaffold for six weeks.
Figure 4:
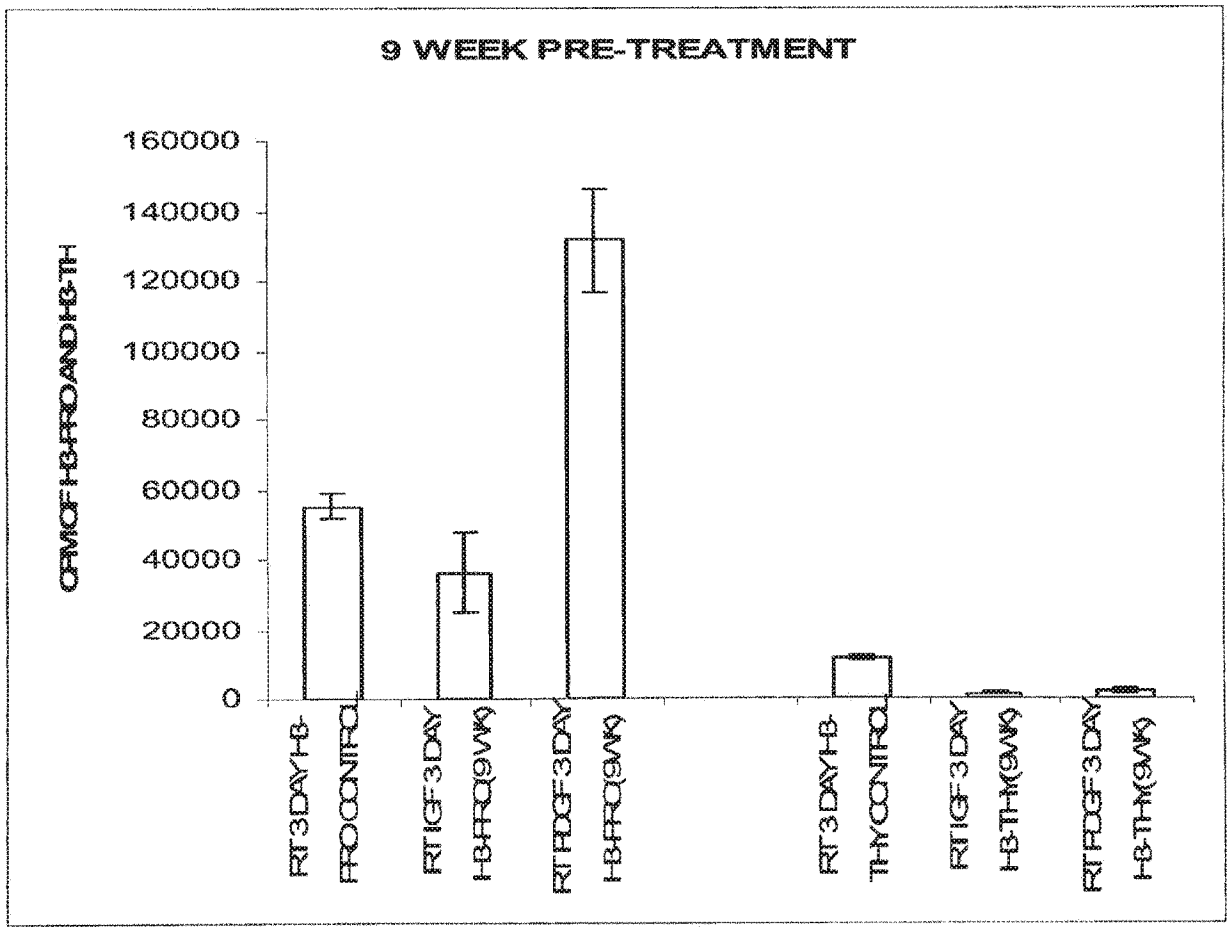
FIG. 4 is a graph showing measurements of collagen (as $^3$H-proline) and DNA (as $^3$H-thymidine) synthesis in naive tendon cells seeded and grown for three days on a scaffold containing killed tendon cells that were transduced with an IGF-1 gene ("IGF"), or a PDGF gene ("PDGF") or no gene ("CONTROL") and grown on the scaffold for nine weeks.

Results are summarized in FIGS. 2-4. Marked stimulation of collagen synthesis in bioactive scaffolds prepared for the six week time period and increasing with the scaffolds examined at the nine week time point (FIGS. 3 and 4).

Example 2

Histological Evaluation of Rat Achilles Tendon Repair Using a Bioactive Scaffold: 2 and 4 Weeks Post-op.

Introduction

Tendon injuries are encountered routinely in orthopaedic practice and cause significant disability in our society. PDGF-β and IGF-1 are potent mitogens that have been shown to augment tendon healing. This two-part study examined the effect of poly(L-lactic acid) (PLLA) scaffolds preconditioned with either wild-type rat tendon fibroblasts (RTF) or growth factor-transduced RTFs on in vitro fibroblast function and in vivo rat Achilles tendon repair.

Study Goals

The ultimate aim of this study was to determine the effect of a novel bioactive scaffold in a rat model of Achilles tendon repair. The goal was to note any increased rates of repair and also to detect any inflammatory response as a result of implantation. This was a two-part study with an in vitro component followed by an in vivo one.

Methods

Both investigations utilized preconditioned scaffolds. RTFs that were either wild-type or transduced with the gene for PDGF-P or IGF-1 were seeded onto PLLA scaffolds and incubated for 3, 6, or 9 weeks. Scaffolds were then frozen at −80° C., lyophilized, and stored to create a unique, "off-the-shelf" bioactive scaffold. In the in vitro study, wild-type RTFs were seeded onto experimental and control scaffolds, cultured for 3 or 7 days, and labeled with markers for collagen and DNA synthesis. In the in vivo study, 24 rats underwent surgical transection of their Achilles tendon and primary repair by either suture alone, suture plus control scaffold, or suture plus preconditioned scaffold. Rats were sacrificed at 2 or 4 weeks, and studied for histological quality of repair.

All surgical procedures were conducted in the laboratory of Dr. Daniel Grande at The Feinstein Institute for Medical Research according to the requirements and approval of the IACUC. All animal procedures were performed according to the PHS guide for the ethical treatment of animal subjects. After sacrificing, rat hind limbs were dissected carefully, leaving the Achilles tendon intact, and connected to both calf muscle and hind claw. The dissected rat hind limbs were then fixed in formalin and preserved until evaluated later. The samples were then stained using hematoxylin and eosin, Mallory's trichrome, and picosirius red.

The following experimental and control groups were utilized in the in vivo portion of this study:

| Group | Time Followed Post-op |
|---|---|
| Suture repair alone | 2, 4 weeks |
| Suture + PLLA scaffold | 2, 4 weeks |
| Suture + PLLA bioactive scaffold With PDGF | 2, 4 weeks |

Histology Grading. The specimens were graded histologically using a modified Soslowsky score evaluating collagen grade (measuring degree of organization), and degree of angiogenesis. The scoring system utilized the following 0-3 score.

| Score | Histological Observation |
|---|---|
| 0 | normal collagen oriented tangentially |
| 1 | mild changes with collagen fibers <25% disorganized |
| 2 | moderate changes with collagen fibers <50% disorganized |
| 3 | marked changes in collagen >50% disorganized. |

Thus, the lower the score the better the outcome.

Results

In vitro study. In the in vitro study, scaffolds preconditioned with either wild-type RTFs or RTFs expressing transgenic growth factor promoted RTF proliferation and collagen synthesis over controls.

In vivo study. In the in vivo study, repairs that included the scaffolds preconditioned with growth factor demonstrated the best overall histological repair. Histologic grading at 2 weeks demonstrated lower scores (indicating better healing) for tendons repaired with sutures augmented with a PLLA bioactive scaffold (prepared with cells expressing PDGF) as compared to controls. The suture alone controls and suture plus PLLA resulted in poorly organized repair tissue. This similar trend continued for the four-week time point also (Table 1).

TABLE I

Collagen grades of rat Achilles tendon as a function of treatment group and time post-op.

| Group | Time Post-op | Collagen Grade |
|---|---|---|
| Suture Alone | 2 weeks | 3.5 |
| | 4 weeks | 4.0 |
| Suture + PLLA | 2 weeks | 3.0 |
| | 4 weeks | 3.3 |
| Suture + PLLA + PDGF | 2 weeks | 1.5 |
| | 4 weeks | 1.5 |

The collagen grades were confirmed by further observation and grading of the repair sites under polarized light after picosirius red staining.

Conclusions. This two-part study demonstrates that scaffolds preconditioned with either wild-type RTFs or growth factor can promote tendon fibroblast function in both an in vitro and in vivo model systems. The ability of these scaffolds to improve tendon repair after being frozen at −80° C., lyophilized, and stored provides "off-the-shelf" convenience in a bioactive scaffold system. There was no immune response noted in the repair tissue surrounding and within the scaffold. The cells migrated throughout the scaffold and appeared to synthesize new matrix rapidly.

Example 3

Detection of Preconditioned Scaffolds in Articular Defects Using Ultrasound Technology Introduction The goal of this study was to evaluate ultrasound as a safe, novel imaging modality for the non-invasive monitoring of the healing response of an osteochondral defect that was treated with implantation of a preconditioned bioactive scaffold, and to correlate the ultrasound imaging with histological observation.

Methods and Materials

Bilateral osteochondral defects were surgically created in the trochlear groove of the knee in fifteen adult male New Zealand white rabbits, under IACUC approval. Twenty-four defects were filled with PLLA scaffolds preconditioned with either IGF-1 or BMP-7 (using the transduced cell technology described above), and eight were left as unfilled controls. The knees were then harvested at 3, 6, and 12 weeks post-surgery, and evaluated with histological evaluation, as compared to ultrasound, using FlexScan image processing software.

Results

Osteochondral defects were clearly identified in each ultrasound performed. Imaging of knees containing an unfilled osteochondral defect demonstrated an empty gap in the trochlear groove, whereas those with a scaffold implant exhibited filling of the defect. Ultrasound images correlate with histologic evaluation in demonstrating a progressive increase in the healing response around osteochondral defects filled with preconditioned bioactive scaffolds for the three, six and twelve week samples.

Conclusions

Ultrasound was able to distinguish the site and borders of both the osteochondral defect and the implanted scaffold, and was accurate in measuring the dimensions of the osteochondral defect and the scaffold within it. Progressive changes in these measurements allow monitoring of the repair tissue in a temporal fashion. Lateral edge integration in the osteochondral defect was also observed with ultrasonography, correlating with histological results.

REFERENCES

Abboud J A, Soslowsky L J. interplay of static and dynamic restraints in glenohumeral instability. Clin Orthop 2002; 1(400):48-57.

Almarza, A J and Athanasiou K A. Design characteristics for the tissue engineering of cartilaginous tissues. Annals Biomed Eng 2004; 32:148-159.

Alper J. Biology and the inkjets. Science 2004; 305; 1895.

Aspenburg P, Forslund C. Enhanced tendon healing with GDF 5 and 6. Acta Orthopa Scand 1999; 70(1):51-54.

Bey M J, Ramsey M L, Soslowsky L J. Intratendinous train field of the supraspinatus tendon: Effect of surgically created articular-surface rotator cuff tear. J Shoulder Elbow Surg 2002; November-December; 11(6):562-9.

Carpenter J E, Thomopoulos S, Flanaga C L, DeBano C M, Soslowsky L J. Rotator cuff defect healing: A biomechanical and histologic analyses in an animal model. J Shoulder Elbow Surgery 1998; 7(6); 599-605.

Carpenter J E, Thomopoulos S, Soslowsky L J. Animal models of tendon and ligament injuries for tissue engineering applications. Clin Orthop 1999 October; (367 Supp): S296-311.

Choi H, Kondo S, Hirose K, Ishiguro N, Hasegawa Y, Iwata H. J. Expression of enzymatic activity of MMP-2 during healing process of the acute supraspinatus tendon tear in rabbits. Journal of Orthop Res 2002; 20:927-933.

Dahigren L A, Nixon A J. And Brower-Toland B D. Effects of beta-aminopropionitrile on equine metabolism in vitro and on effects of insulin-like growth factor-I on matrix production by equine tenocytes. Am J Vet Res 2001; 62(10): 1557-62.

Dahlgren L A, van der Meulen M C, Bertram J E., Starrak G S., and Nixon A J. Insulin-like growth factor-I improves cellular and molecular aspects of healing in a collagenase-induced model of flexor tendinitis, J Ortho Res 2002; 20(5):910-9.

Desmouliere A Geinoz A Gabbiani F5 and Gabbiani G. Transforming growth factor b1 induces a1 smooth muscle actin expression in granulation tissue myofibroblasts and in quiescent and growing cultured fibroblasts. J Cell Biol 1993; 192:103-111.

Frenkel S R and DiCesare P E. Scaffolds for articular cartilage repair. Annals Biomed Eng 2004; 32:26-34.

Hardwood F L, Goomer R S., Gelberman R H., Silva M J., and Ameil D. Regulation of alpha(v) beta 3 and alpha 5 beta integrin receptors by basic fibroblast growth factor and platelet-derived growth factor-BB in intrasynovial flexor tendon cells. Wound Repair Regen 1999; 7(5):381-8.

Jann H W, Stein L E., and Slater D A. In vitro effects of epidermal growth factor or insulin-like growth factor on tenoblast migration on absorbable suture material. Vet Surg 1999; 28(4):268-78.

Kobayashi K, Hamada K, Gotoh M, Handa A, Yamakawa H, Fukuda H. Healing of full-thickness tears of avian supracoracoid tendons: in situ hybridization of a1(I) and a1 (111) procollagen mRNA. J Ortho Res 2001; 19:862-868.

Lewis C W5 Schlegel T F, Hawkins R J, James S P, Turner A. The effects of immobilization on rotator cuff healing using modified Mason-Allen stitches: a biochemical study in sheep. Biomed Sci Instrum 2001: 37:263-8.

Li W-C, Yu W-Y, Quinlan J M, Burke 7 D, Tosh D. The molecular basis of transdifferentiation. J Cell Mol Med 2005; 9:569-582.

Malickey D M, Kuhn J E, Frisancho J C, Lindholm S R, Raz J A, Soslowsky L J. Nonrecoverable strain fields of the anteroinferior glenohumeral capsule under subluxation. J Shoulder Elbow Surg 2002 November-December; 111(6): 529-540.

Nakase T, Sugamoto K, Miyamoto T, Tsomaki N, Luyten F, Inui H, Myoui A, Tomita T, Yoshikawa H. Activation of cartilage derived Morphogenic protein-1 in torn rotator cuff. Clin Ortho Rel Res 2002; 399:140-145.

Premdas J, Tang J B, Warner J P, Murray M M, Spector M. The presence of smooth muscle actin in fibroblast32s in the torn human rotator cuff. J Ortho Res 2001; 19:221-228.

Rickert M, Jung M, Adiyaman M, Richter W, Simank H G. A growth and differentiation factor-5 (GDF-5)-coated suture stimulates tendon healing in an Achilles tendon model in rats. Growth Factors 2001; 19(2): 115-26.

Sharma B and Elisseeff J H. Engineering structurally organized cartilage and bone tissues. Annals Biomed Eng 2004; 32:148-159.

Skutek M., van Griensven M., Zeichen J., Brauer N., and Bosch U. Cyclic mechanical stretching modulates secretion pattern of growth factors in human tendon fibroblasts. European J Appl Physiol 2001; 86(1):48-52.

Soslowsky L J, Carpenter J E, Bucchieri J S, Flatow E L. Biomechanics of the rotator cuff. Orth Clin NA 1997; 28:17.

Thomopoulos S, Hattersley G, Rose V, Mertens M, Galatz L, Williams G R, Solowsky L J. The localized expression of extracellular matrix components in healing tendon insertion sites: an in situ hybridization study. J Ortho Res 2002; 20:454-463.

Wada, Kubota H, Akiyama T, Hatanka H, Miura H, Iwamoto Y. Effects of absorbable polydioxanone flexor tendon repair and restricted active mobilization in a canine model. J Hand Surg [AM] 2001; May; 26(3)398-406.

Yoshikawa Y, and Abrahamson S O. Dose-related cellular effects of platelet-derived growth factor-BB differ in various types of rabbit tendons in vitro. Acta Orthopaedica Scandinavica 2001: 72(3):287-92.

PCT Publication WO99/43787.

PCT Publication WO03/041568.

PCT Publication WO03/043486.

PCT Publication WO03/044164.

PCT Publication WO03/082 145.

US Patent Application Publication 2003/0068817.

US Patent Application Publication 2004/0078090.

US Patent Application Publication 2004/0175366.

U.S. Pat. No. 4,846,835.

U.S. Pat. No. 5,700,289.

U.S. Pat. No. 5,906,934.

U.S. Pat. No. 6,214,369.

U.S. Pat. No. 6,398,816.

U.S. Pat. No. 6,737,053.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A tissue scaffold comprising mammalian cells which have colonized the scaffold, wherein the mammalian cells are transgenic cells in that they comprise a first transgenic bioactive molecule, and wherein the transgenic cells are treated, after colonization of the scaffold, so that they are unable to undergo mitosis.

2. The tissue scaffold of claim 1, wherein the transgenic cells are killed by freezing then thawing the transgenic cells.

3. The tissue scaffold of claim 1, wherein the tissue scaffold is lyophilized.

4. The tissue scaffold of claim 2, wherein the tissue scaffold is lyophilized after the transgenic cells have been killed by freezing then thawing.

5. The tissue scaffold of claim 1, wherein the first transgenic bioactive molecule is a bone growth factor, a nerve growth factor, a cartilage growth factor, a growth factor affecting wound healing, or a growth factor affecting tissue repair.

6. The tissue scaffold of claim 5, wherein the first transgenic bioactive molecule is a platelet-derived growth factor (PDGF), a vascular endothelial growth factor (VEGF), an epidermal growth factor (EGF), a basic fibroblast growth factor (FGF), an insulin-like growth factor (IGF), an endothelial derived growth supplement (EDGS), a keratinocyte growth factor (KCF), an osteogenin, a skeletal growth factor (SGF), a bone-derived growth factor (BDGFs), a retinoid, a growth hormone (GH), a bone morphogenic protein (BMP), a transcription factor, a member of the hedgehog family, or a transferrin.

7. The tissue scaffold of claim 5, wherein the first transgenic bioactive molecule is a bone morphogenic protein (BMP), a TGF-β, or an insulin-like growth factor (IGF).

8. The tissue scaffold of claim 5, wherein the first transgenic bioactive molecule is a PDGFβ or an IGF-1.

9. The tissue scaffold of claim 1, wherein the mammalian cells further comprise a second transgenic bioactive molecule.

10. The tissue scaffold of claim 1, wherein the mammalian cells are human cells.

11. The tissue scaffold of claim 1, wherein the cells are nerve cells, epidermal cells, dermal cells, periosteal cells, epithelial cells, endothelial cells, tendon cells, embryonic stem cells, adult stem cells, osteoblasts, myoblasts, chondrocytes, or fibroblasts.

12. The tissue scaffold of claim 1, wherein the scaffold is derived from a vertebrate.

13. The tissue scaffold of claim 1, wherein the scaffold is artificial.

14. The tissue scaffold of claim 13, wherein the scaffold comprises at least one of collagen, alginate, chitosan, poly (paradioxanone), poly(lactic acid), poly(glycolic acid), or a copolymer of poly(lactic acid) and poly(glycolic acid).

15. The tissue scaffold of claim 1, wherein the scaffold further comprises additional vertebrate cells seeded onto the scaffold, wherein the additional vertebrate cells are alive.

16. The tissue scaffold of claim 15, wherein the additional vertebrate cells do not express a transgenic bioactive molecule.

17. The tissue scaffold of claim 15, wherein the additional vertebrate cells express an additional transgenic bioactive molecule.

18. The tissue scaffold of claim 17, wherein the additional transgenic bioactive molecule is a protein or a nucleic acid.

19. The tissue scaffold of claim 17, wherein the additional transgenic bioactive molecule is a protein.

20. The tissue scaffold of claim 19, wherein the additional transgenic bioactive molecule is an enzyme, a cytokine, a marker protein or an antibody.

21. The tissue scaffold of claim 17, wherein the additional transgenic bioactive molecule is a nucleic acid.

22. The tissue scaffold of claim 21, wherein the nucleic acid is an RNAi molecule, a ribozyme, as antisense molecule, or an aptamer.

23. The tissue scaffold of claim 17, wherein the additional transgenic bioactive molecule is constitutively expressed.

24. The tissue scaffold of claim 17, wherein the additional transgenic bioactive molecule is operably linked to an inducible promoter.

25. The tissue scaffold of claim 15, wherein the additional vertebrate cells are capable of mitosis.

26. A method of tissue repair in a mammal, the method comprising implanting the tissue scaffold of claim 1 into the tissue in the mammal, wherein the tissue is bone, cartilage, nerve or tendon tissue.

27. A method of delivering a first transgenic bioactive molecule to a tissue of a mammal, the method comprising implanting the tissue scaffold of claim 1 into the mammal in or adjacent to the tissue.

28. A method of making the tissue scaffold of claim 1, the method comprising seeding a scaffold with mammalian vertebrate cells comprising a transgene encoding a first bioactive molecule, incubating the scaffold under conditions and for a time sufficient for the mammalian cells to colonize the scaffold and express the first transgenic bioactive molecule, and treating the mammalian cells colonizing the scaffold such that the cells are unable to undergo mitosis.

29. the method of claim 28, wherein the mammalian vertebrate cells colonizing the scaffold are treated by freezing and thawing.

30. The method of claim 29, wherein the scaffold is lyophilized after the step of freezing and thawing the cells.

31. The method of claim 28, wherein the scaffold is subsequently seeded with additional vertebrate cells, wherein the additional vertebrate cells are alive.

32. The method of claim 28, wherein the vertebrate cells are human cells.

33. The method of claim 31, wherein the additional vertebrate cells are human cells.

* * * * *